United States Patent [19]

Preston et al.

[11] Patent Number: 4,516,857
[45] Date of Patent: May 14, 1985

[54] CORRELATION SPECTROMETER FOR NERVE AGENTS

[75] Inventors: John M. Preston, Ottawa; Thomas V. Ward, Thornhill; William H. Morrow, Cookstown, all of Canada

[73] Assignee: Her Majesty the Queen in right of Canada, as represented by the Minister of National Defence, Canada

[21] Appl. No.: 374,701

[22] Filed: May 4, 1982

[30] Foreign Application Priority Data

May 4, 1981 [CA] Canada ................................. 376763

[51] Int. Cl.³ ........................................... G01N 21/61
[52] U.S. Cl. ...................................... 356/418; 356/51; 250/343
[58] Field of Search ................ 356/51, 418; 250/339, 250/343; 340/632

[56] References Cited

U.S. PATENT DOCUMENTS 3,194,962  7/1965  Carlon et al. .................. 250/343 X

FOREIGN PATENT DOCUMENTS 1104636  2/1968  United Kingdom .
1318472  4/1971  United Kingdom .
1237547  6/1971  United Kingdom .
1429198  3/1976  United Kingdom .

*Primary Examiner*—F. L. Evans
*Attorney, Agent, or Firm*—Murray, Whisenhunt & Ferguson

[57] ABSTRACT

A correlation spectrometer directs light from the ambient atmosphere onto a light detector, a first portion of the light being directed through a reference substance and a second portion being directed onto said light detector without passage through the reference substance, whereby the light detector provides first and second electrical signals corresponding, respectively, to said first and second light portions. The reference substance is a surrogate substance different from a substance to be detected by the spectrometer but which has a spectrum which correlates with that of the substance to be detected.

16 Claims, 3 Drawing Figures

CORRELATION SPECTROMETER FOR NERVE AGENTS

The present invention relates to a correlation spectrometer and is useful, in particular, for the detection of highly toxic compounds such as chemical warfare agents.

A conventional correlation spectrometer operates by the passage of light, either ambient or generated, through an atmospheric path which may contain one or more compounds of interest, and then through two paths inside the spectrometer, one of the paths containing a sample of the compound or compounds to be detected and the other path containing a neutral absorber. By comparison of the corresponding electrical signals, a difference signal is provided which serves to indicate the presence or otherwise of the compound or compounds of interest in the external atmospheric path.

However, for the detection of nerve agents, for example by recognizing a prominent spectral feature common to organophosphate esters, the very high toxicity of these compounds prevents the use of a sample thereof in a spectrometer. Also, the low vapour pressures of such compounds makes it impractical to have vapour samples in a spectrometer.

It is accordingly an object of the present invention to provide a novel and improved correlation spectrometer which functions without the presence therein of a substance to be detected.

According to the present invention, there is provided, in a correlation spectrometer comprising light responsive means for providing electrical signals; means for directing light from the ambient atmosphere onto the light responsive means; the light directing means comprising means for passing a first portion of the light onto the light responsive means through a reference substance and for passing a second portion of the light onto the light responsive means without passage through the reference substance, whereby the light responsive means provides first and second electrical signals corresponding respectively, to the first and second light portions; and signal processing means for comparing the first and second electrical signals; the improvement that the reference substance is a surrogate substance different from a substance to be detected by the spectrometer but which has a spectrum which correlates with that of the substance to be detected.

The invention will be more readily understood from the following description of a preferred embodiment thereof given, by way of example, with reference to the accompanying diagrammatic drawings, in which.

Figure 1:
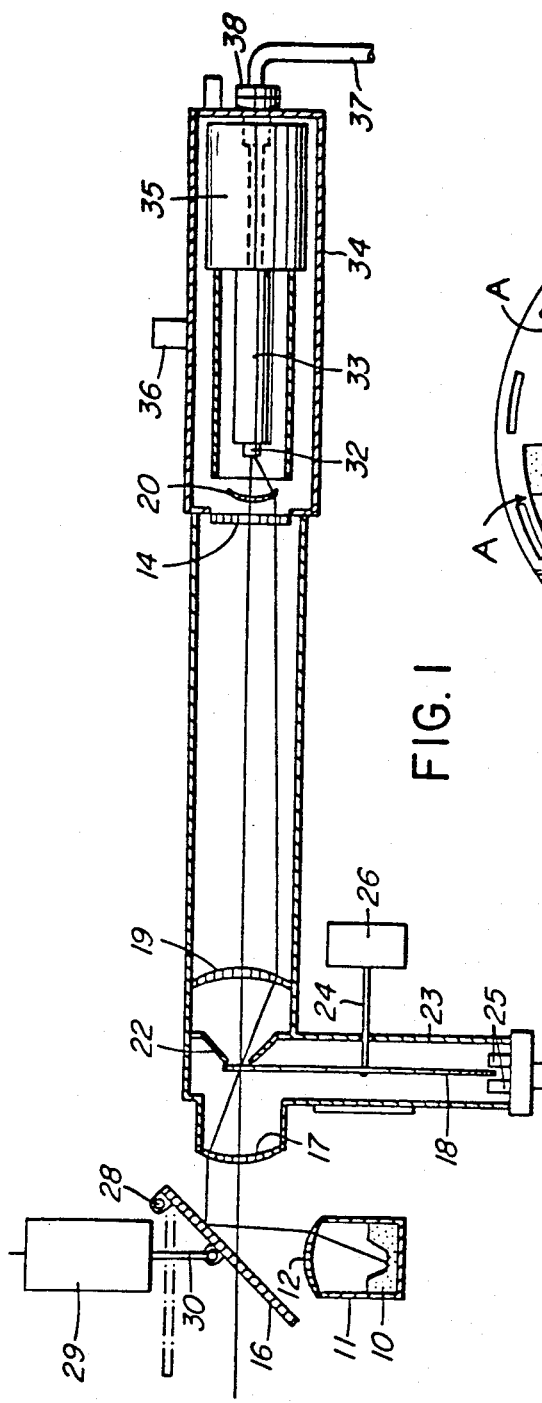
FIG. 1 shows a side view of the optical system of a corelation spectrometer.

Referring firstly to FIG. 1 of the accompanying drawings, the optical system illustrated therein has a reference radiation source in the form of a thermal or black body source 10, which is hermetically enclosed in a housing or insulated can 11 provided with a lens 12, which magnifies the black body source so as to fill the sensor field of a lead-tin-telluride detector indicated generally by reference numeral 32.

The radiation passing through the lens 12 is reflected by an angled reflector mirror 16 so as to pass through an objective lens 17, which focuses this radiation on a correlation or chopping disc 18.

As described in greater detail below, the correlation disc 18 is provided with a plurality of apertures, and the light passing through these apertures is deflected by a transfer lens 19 through an interference filter 14 onto a detector lens 20 forming part of the detector 32. The interference filter 14 limits the light reaching the detector 32 to a wavelength region selected to optimize the correlation.

Immediately after the correlation disc 18, the light passes through a light stop 22, which defines the field of view of the spectrometer.

The correlation disc 18 is enclosed in an insulated housing 23, which is hermetically sealed by the objective lens 17 and the transfer lens 19, and by a Teflon bushing (not shown) on a shaft 24 provided for rotating the correlation disc 18. The enclosure of the correlation disc 18 in the housing 23 serves to damp out short term temperature drift. Within the housing 23, a pair of slotted optical switches 25 cooperate with the peripheral portion of the correlation disc 18 to provide synchronizing signals, for the purpose described below.

The shaft 24 is driven, for rotating the correlation disc 18, by a four pole d.c. brushless motor 26.

The mirror 16 is pivotally mounted, adjacent one edge thereof, by means of a pivot pin 28, and a solenoid 29 is pivotally connected by an arm 30 to the mirror 16 for pivoting the mirror 16, about the axis of the pivot 28, between a first position, in which the mirror 16 is shown in full lines in FIG. 1, and a second, horizontal position, shown in broken lines in FIG. 1. When the mirror 16 is in this second position, light from the ambient atmosphere can enter the spectrometer through the objective lens 17 for detection by the detector 32, and the transmission of light from the black body source 11 to the detector 32 is interrupted.

The black body source 10 comprises a resistance heater provided with proportional temperature control using a thermistor temperature monitor (not shown). By employing the lens 12 to fill the field of view of the detector 32, a large effective black body aperture is obtained with a relatively small black body area, thus providing the advantage of lower power consumption.

The detector 32 is provided with a cryostat 33 and housed within an electromagnetically shielded and hermetically sealed detector housing 34, which also contains a preamplifier 35 and is provided with a pressure relief valve 36. Dry argon gas is supplied into the interior of the detector housing 34 from a pipe 37 through a quick disconnect coupling 38 and is maintained, by the pressure relief valve 36, at a slight positive pressure within the detector housing 34, the argon being supplied to the pipe 37 from a spherical tank (not shown) through a molecular sieve drying filter (not shown).

Figure 2:
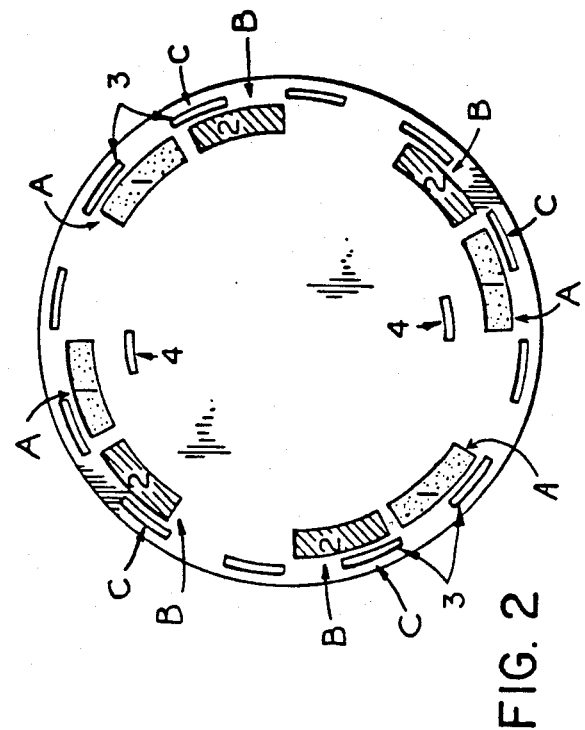
FIG. 2 shows a correlation disc forming part of the spectrometer of FIG. 1.

Referring now to FIG. 2, the correlation or chopper disc 18 is made of aluminum and is divided equally into four sectors, each sector being subdivided into three sub-sectors A, B and C. The sub-sectors A include apertures 1 containing a surrogate reference material in the form of a foil. The sub-sectors B include apertures 2 which may contain a second reference material, also in the form of a foil, which correlates with the substance or compound being searched for with the opposite sign, or may be empty, or may contain a neutral (i.e., no spectral character) absorber. Sub-sectors C are opaque and blackened portions of the chopper disc 18 and serve to allow monitoring the intensity of ambient radiation passing through apertures 1 and 2 on each occasion in spite of a.c. coupling following the detector 32

In use, the rising edge of the signal from light transmitted through apertures 3 is used to trigger a counter (not shown), which counts for a period long enough that the apertures (1 and 2) are not obscured by any portion of the wheel. The end of this count starts a second counter (not shown), whose duration is used for sampling the light intensity. This ensures the required reproducibility in sampling times. Apertures 4 are provided in the correlation disc 18 to provide synchronizing signals for indicating which sector is presently in view.

Figure 3:
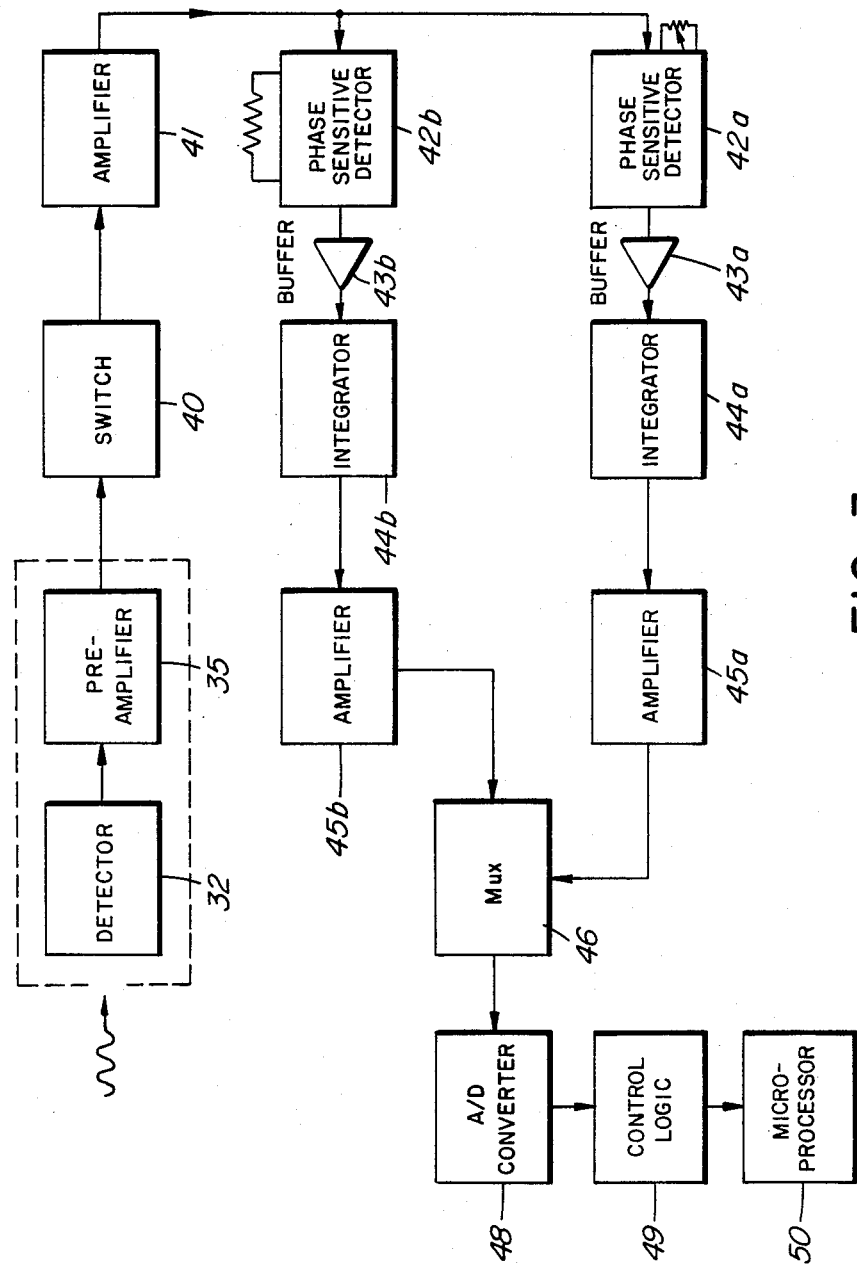
FIG. 3 shows a block diagram of signal processing components for the spectrometer of FIG. 1.

Referring now to FIG. 3, the output of the preamplifier 35 is connected through an in-line switch 40 to an amplifier 41.

The output of the amplifier 41 is connected to two phase sensitive detectors 42a and 42b which, in turn, are connected through buffers 43a, 43b; integrators 44a, 44b and amplifiers 45a and 45b, respectively, to multiplexer 46.

The output of the multiplexer 46 is connected through an analog-to-digital converter 48 and control logic 49 to a microprocessor 50, which in the present embodiment is a microprocessor Model No. Z80 made by Zilog but may be replaced by any other suitable microprocessor.

The operation of the above-described apparatus is as follows:

The mirror 16 is normally pivoted into the horizontal position, so that light from the ambient atmosphere passes through the sectors 1 and 2 of the rotating correlation disc 18 to the detector 32.

The output of the detector 32 is amplified by the preamplifier 35 and switch 40, controlled by the synchronizing slots in the correlation disc 18, ensures that the output of the preamplifier 35 is interrupted except when one of the sectors 1 and 2 fully occupies the field of view of the light stop 22. The phase-sensitive detectors 42a, 42b form two difference signals, one of which is proportional to the difference in intensities transmitted by apertures 1 and 2, and the other being proportional to the difference between either 1 or 2 and the opaque sub-sector C.

These signals are integrated by the integrators 44a, 44b to improve the signal-to-noise ratio, amplified by the amplifiers 45a and 45b and multiplexed by the multiplexer 46.

The outputs of the multiplexer 46 converted by the analog-to-digital converter 48 and fed into the microprocessor 50 under the control of the control logic 49.

The microprocessor 50 computes a value indicative of the presence of the substance or compound being searched for, when it is present.

This value is computed by calculating the absolute value of the difference in intensities passing through apertures 1 and 2. Firstly, however, emission by the materials themselves must be accounted for.

To enable the data processing to compensate for emission of light by the reference sample or surrogate substance, the spectrometer must occasionally view the constant temperature black body 10, which is effected by energizing the solenoid 29 to pivot the mirror 16 into the position shown in solid lines in FIG. 1, e.g. for a period of 0.5 secs. at intervals of 15 secs.

To enable an alarm to be triggered regardless of the temperature of the background, since for example a hillside is considerably warmer and emits more intensely through clear sky, the signal corresponding to the intensity difference between the apertures 1 and 2 is multiplied by an exponential function of the intensity difference between the background and the opaque sectors C of the chopping wheel 18.

The surrogate reference material contained in the apertures 1 may be a polymeric foil for example poly(4-methyl styrene), which over a predetermined wavelength has a spectrum similar to organophosphate esters, including most antichloinesteric insecticides and the known nerve agents.

The second reference substance which, as indicated above, may be contained in the sectors 2 and which has a spectrum which correlates negatively with the substance to be detected may in that case comprise a film of poly(4-iodo styrene). The use of this second reference substance increases the magnitude of the above-mentioned difference signal without increasing noise.

We claim:

1. A correlation spectrometer for the detection of a toxic substance in the atmosphere comprising:
   light responsive means for providing electrical signals;
   means for directing ambient light onto said light responsive means;
   said light directing means comprising means for passing a first portion of the light onto said light responsive means through a solid reference substance in the form of a foil and for passing a second portion of the light onto said light responsive means without passage through the reference substance, whereby said light responsive means provides first and second electrical signals corresponding respectively, to said first and second light portions; and
   signal processing means for comparing said first and second electrical signals;
   wherein said reference substance is a surrogate substance different from the toxic substance to be detected by the spectrometer but which has a spectrum which correlates with that of the toxic substance to be detected.

2. A correlation spectrometer as claimed in claim 1, wherein said reference substance has a spectrum similar to the substance to be detected over at least a predetermined range of wavelength.

3. A correlation spectrometer as claimed in claims 1 or 2, wherein said reference substance comprises poly(4-methyl styrene).

4. A correlating spectrometer as claimed in claim 1, wherein an additional reference substance having a spectrum which correlates negatively with the substance to be detected is disposed in the path of said second light portion.

5. A correlation spectrometer as claimed in claim 4, wherein said additional reference substance comprises poly (4-iodostyrene).

6. A correlation spectrometer as claimed in claim 1, further comprising a correlation disc having first and second apertures distributed around said disc and means for rotating said disc, said apertures being disposed for movement in succession across the path of light on rotation of said disc, the first apertures containing said reference substance and said first and second apertures being arranged in the sequence 1, 2, 2, 1, 1, 2, 2, 1; where 1 represents said first apertures and 2 represents said second apertures.

7. A correlation spectrometer as claimed in claim 6, wherein said disc further comprises opaque blackened portions and wherein said apertures and said blackened portions are arranged in the sequence 1, 2, 3, 2, 1, 3, 1, 2, 3, 2, 1, 3 where 3 represents said opaque blackened portions.

8. A correlation spectrometer as claimed in claim 6, wherein said second apertures contain an additional reference substance in the form of a foil, and wherein said additional reference substance provides a spectrum which correlates negatively with the substance to be detected.

9. A correlation spectrometer as claimed in claims 6, 7 or 8, wherein said correlation disc is mounted in a hermetically sealed housing.

10. A correlation spectrometer as claimed in claims 6, 7 or 8, wherein said light directing means comprise an optical system including objective lens means for focusing the light onto the plane of said disc, a field stop adjacent said disc and transfer lens means for collimating the light transmitted through said disc apertures and said field stop to said light responsive means.

11. A correlation spectrometer as claimed in claim 1, further comprising a reference radiation source for emitting light of known characteristics, and light control means for temporarily interrupting the passage of ambient light through said reference substance while directing therethrough said light of known characteristics to allow correction for light emission by said reference substance.

12. A correlation spectrometer as claimed in claim 11, wherein said reference radiation source comprises a black body; and wherein said light control means comprises pivotally mounted reflector means for directing radiation from said black body to said correlation disc in a first position of said reflector means; means for pivoting said reflector means between said first position and a second position in which said reflector means is removed from a light path from the ambient atmosphere to said correlation disc; and means hermetically sealing said black body; said sealing means including objective lens means for filling the field of view of said light responsive means with the radiation when said reflector means is in said first position.

13. A correlation spectrometer as claimed in claim 11, further comprising means for deriving a further difference signal proportional to the difference between the ambient light and the light of known characteristics and means for modifying the output of said signal processing means in accordance with said further difference signal to provide a corrected indication of the presence, absence or quantity of the substance to be detected.

14. A correlation spectrometer as claimed in claim 13, wherein said output modifying means comprise means for deriving an exponential function of said difference signal and means for multiplying said output by said exponential function.

15. A correlation spectrometer as claimed in claim 6, wherein said second apertures are empty.

16. A correlation spectrometer as claimed in claims 11, 12 or 15, wherein said toxic substance is an organophosphate ester.

* * * * *